United States Patent [19]

Ito et al.

[11] Patent Number: 5,420,348

[45] Date of Patent: May 30, 1995

[54] UREA DERIVATIVES AND SALTS THEREOF

[75] Inventors: Noriki Ito, Saitama; Koyo Matsuda, Ibaraki; Kiyoshi Iwaoka, Ibaraki; Yuichi Iizumi, Ibaraki, all of Japan

[73] Assignee: Yamanouchi Pharmaceutical Co., Ltd., Tokyo, Japan

[21] Appl. No.: 86,689

[22] Filed: Jul. 2, 1993

Related U.S. Application Data

[63] Continuation of Ser. No. 953,755, Sep. 29, 1992, Pat. No. 5,258,405, which is a continuation of Ser. No. 831,871, Feb. 5, 1992, abandoned, which is a continuation-in-part of Ser. No. 666,721, Mar. 8, 1991, abandoned.

[30] Foreign Application Priority Data

Mar. 12, 1990 [JP] Japan .................................. 2-60754

[51] Int. Cl.$^6$ .......................................... C07C 275/26
[52] U.S. Cl. .......................................... 564/48; 564/50; 564/53; 564/54
[58] Field of Search ...................... 564/48, 50, 53, 54; 514/596, 597

[56] References Cited

U.S. PATENT DOCUMENTS 4,405,644  9/1983  Kabbe et al. ..................... 514/596

OTHER PUBLICATIONS

Ranise et al, Chemical Abstracts, vol. 109 (1988) 445t.

*Primary Examiner*—Richard L. Raymond
*Attorney, Agent, or Firm*—Burgess, Ryan & Wayne

[57] ABSTRACT

Urea derivatives of the general formula (I)

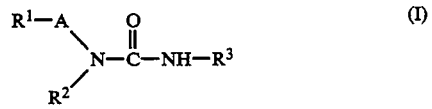

and salts thereof, pharmaceutical compositions containing the same, and methods for producing the same are-disclosed.

The urea derivatives of the general formula (I) and salts thereof are novel compounds having the acyl-CoA cholesterol acyltransferase (ACAT) inhibiting activity.

12 Claims, No Drawings

UREA DERIVATIVES AND SALTS THEREOF

RELATED APPLICATIONS

This application is a continuation of Ser. No. 07/953,755, filed Sep. 29, 1992, now U.S. Pat. No. 5,258,405, which is a continuation of Ser. No. 07/831,871, filed Feb. 5, 1992, now abandoned, which in turn is a continuation-in-part of Ser. No. 07/666,721, filed Mar. 8, 1991, now abandoned.

FIELD OF THE INVENTION

The present invention relates to urea derivatives of the following general formula (I) and salts thereof, which are of value as drugs for the treatment and prevention of various diseases related, particularly to atherosclerosis.

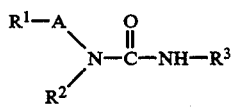 (I)

wherein $R^1$ represents a condensed carbocyclic group containing at least 11 carbon atoms; $R^2$ represents a cycloalkyl group which may optionally have bridgeheads; $R^3$ represents a phenyl group which may optionally be substituted by one or more substituents selected from the group consisting of halogens, lower alkyl groups, amino, and mono- or di-lower alkylamino groups or a tetrahydronaphthyl group; A represents a single bond or a straight-chain or branched alkylene group containing 1 to 6 carbon atoms. The present invention further relates to pharmaceutical compositions containing the compound (I) or a pharmaceutically acceptable salt thereof, and processes for producing the compound (I) or a salt thereof.

BACKGROUND OF THE INVENTION

It is known that accumulation of cholesterol in the vascular system is an etiologic factor in various diseases such as coronary heart disease. Atherosclerosis, among them, is a form of arteriosclerosis which is characterized by the deposition of lipids, particularly cholesterol esters, on the walls, and the resulting thickening, of medium- and large-sized arteries.

It has recently been made clear that the production of such cholesterol ester is catalyzed by acyl-CoA cholesterol acyltransferase (ACAT). Thus, the excessive accumulation of cholesterol ester on the arterial wall is related to an increase in the ACAT enzyme level. Therefore, it is thought that if the ACAT enzyme is successfully inhibited, the esterification reaction of cholesterol will be retarded and the development and progression of atheromatous lesions due to excessive accumulation of cholesterol ester on the arterial wall be successfully prevented.

On the other hand, cholesterol in diets is absorbed as unesterified cholesterol, esterified by the action of ACAT in the body and released into the bloodstream in the form of chylomicrons. Therefore, inhibition of ACAT would suppress not only absorption of dietary cholesterol from the intestinal tract but also reabsorption of the cholesterol released into the intestine.

GB-A-2 113 684 discloses a series of antiatherosclerotic agents which are certain substituted urea and thiourea compounds having ACAT-inhibiting activity.

EP-A-0 335 375 also discloses a series of antihyperlipidemic and antiatherosclerotic agents which are certain substituted urea compounds having ACAT-inhibiting activity.

SUMMARY OF THE INVENTION

An object of the present invention is to provide urea derivatives of the above general formula (I) and salts thereof.

Another object of the invention is to provide processes for producing the urea derivatives of the general formula (I) and salts thereof.

Still another object of the invention is to provide pharmaceutical compositions containing a urea derivative of the general formula (I) or a pharmaceutically acceptable salt thereof.

The compounds (I) according to the present invention are structurally different from the known compounds mentioned above and as has been fully demonstrated in the comparative pharmacological investigations described hereinafter, have markedly superior pharmacologic activity than any of the known compounds.

The compounds (I) according to the present invention is structurally characterized in that a urea derivative is directly attached to a condensed carbocyclic nucleus with or without interposition of an alkylene group.

DETAILED DESCRIPTION OF THE INVENTION

Referring to the definitions of the general formula (I), the "condensed carbocyclic group containing at least 11 carbon atoms" includes, among others,

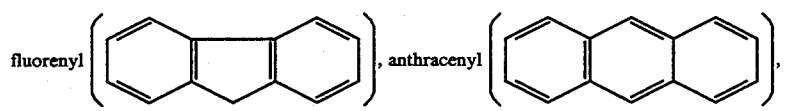

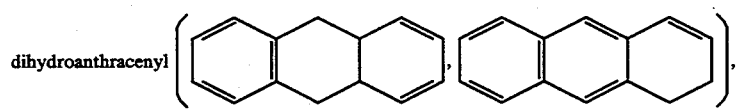

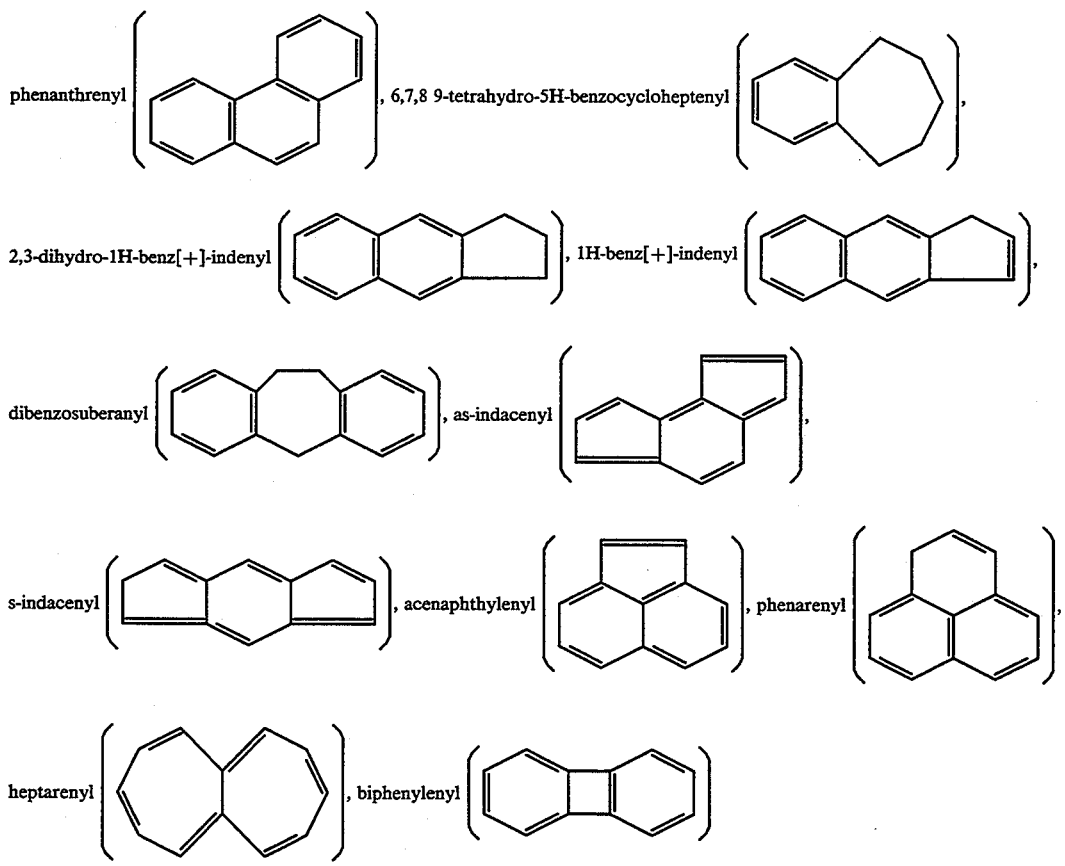

and the like.

The "cycloalkyl group which may optionally have bridgeheads" is a cycloalkyl group containing 3 to 18 carbon atoms, such as cyclopropyl, cyclobutyl, cyclopentyl, cyclohexyl, cycloheptyl, cyclooctyl, cyclononyl, cyclodecyl, cyclododecyl, cyclotridecyl, cyclopentadecyl, adamantyl, norbornyl and so on, and more preferably includes cycloalkyl groups containing 6 to 10 carbon atoms.

Referring to the "phenyl group which may optionally be substituted by one or more substituents selected from the group consisting of halogens, lower alkyl groups, amino, and mono- or di-lower alkylamino groups", the halogen may be chlorine, fluorine, bromine or iodine; the lower alkyl group is a straight-chain or branched alkyl group containing 1 to 5 carbon atoms such as methyl, ethyl, propyl, isopropyl, butyl, isobutyl, sec-butyl, tert-butyl, pentyl (amyl), isopentyl, tert-pentyl, neopentyl, 1-methylbutyl, 2-methylbutyl, 1,2-dimethylpropyl, etc.; and the mono- or di-lower alkylamino group may be an amino group substituted by one or two lower alkyl groups mentioned above.

One or more, whether the same or different, of these halogens and lower alkyl, amino, and mono- or di-lower alkylamino groups may be present on the phenyl group.

Such substituted phenyl group includes, among others, 2,4,6-trifluorophenyl, 2,6-dimethylphenyl, 2,6-diethylphenyl, 2,4,6-trimethylphenyl, 2,4,6-triethylphenyl, 4-propylphenyl, 2,6-diisopropylphenyl, 4-t-butylphenyl, 4-dimethylaminophenyl and the like.

The compound of the general formula (I) may form salts, and such salts are also included within the scope of the present invention. Among such salts are acid addition salts with inorganic acids, such as hydrochloric acid, hydrobromic acid, hydriodic acid, sulfuric acid, nitric acid, phosphoric acid, etc., and acid addition salts with organic acids, such as formic acid, acetic acid, oxalic acid, citric acid, succinic acid, fumaric acid, maleic acid, malic acid, tartaric acid, methanesulfonic acid, ethanesulfonic acid and so on.

As mentioned hereinbefore, the present invention also provides processes for producing the compounds (I) and salts thereof. Some representative processes are described below.

Process 1

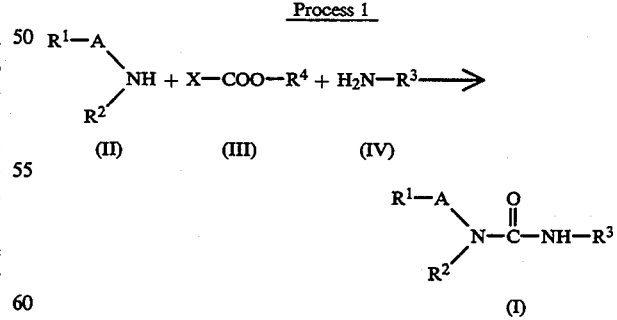

In the above reaction formula, $R^1$, $R^2$, $R^3$ and A are as defined above, X represents a halogen atom and $R^4$ represents a phenyl group or a lower alkyl group.

The compound (I) can be prepared by reacting the compounds of the general formulae (II), (III) and (IV) either concurrently or in an optional order. Preferably, the compound (I) can be produced by reacting an amino compound of the general formula (IV) with a haloformic acid ester of the general formula (III) and reacting the resulting carbamic ester with a compound of the general formula (II).

The haloformic acid ester of the general formula (III) includes isobutyl chloroformate, methyl chloroformate, methyl bromocarbonate, phenyl chloroformate and the like. There are cases in which the reaction can be advantageously hastened using a base such as potassium carbonate, sodium carbonate, sodium hydroxide, potassium hydroxide, triethylamine, N,N-dinethylaniline and the like.

The reaction solvent may be virtually any inert solvent, such as N,N-dimethylformamide, chloroform, benzene, toluene, xylene, dioxane, ether, tetrahydrofuran, chloroform, dichloromethane, dichloroethane and so on. In regard to reaction temperature, the reaction between amino compound (IV) and haloformic acid ester (III) is conducted under cooling or at room temperature and the reaction between the resulting carbamic acid ester and compound (II) is conducted at room temperature or under warming.

Process 2

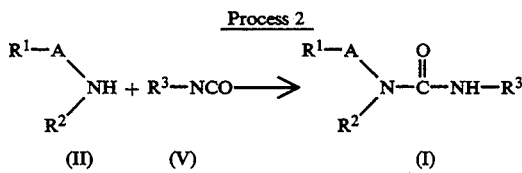

In the above reaction formula, $R^1$, $R^2$, $R^3$ and A are as defined above.

The compound (I) according to the present invention can also be produced by reacting an amino compound of the general formula (II) with an isocyanate compound of the general formula (V). The isocyanate compound (V) is used generally in an equimolar amount with respect to the Compound (II).

This reaction is conducted in an inert solvent, such as N,N-dimethylformamide, pyridine, benzene, toluene, dioxane, tetrahydrofuran, ether, chloroform, dichloromethane, dichtoroethane, n-hexane, etc., at room temperature or with heating.

Process 3

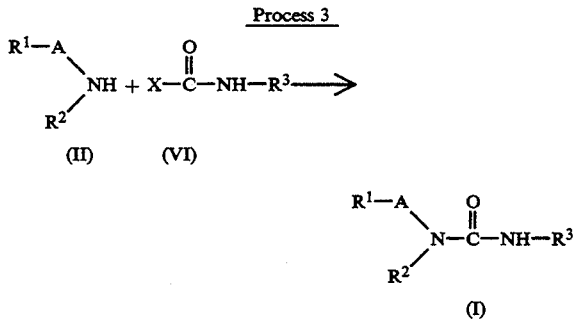

In the above reaction formula, $R^1$, $R^2$, $R^3$ and A are as defined above, and X represents a halogen atom.

The compound (I) of the present invention can also be produced by reacting an amino compound of the general formula (II) with a halogen compound of the general formula (VI).

This reaction is conducted by reacting amino compound (II) with halogen compound (VI) in equimolar proportions in an inert solvent such as N,N-dimethylformamide, benzene, toluene, dioxane, tetrahydrofuran, ether, chloroform, dichloromethane, dichloroethane, n-hexane and so on. The reaction temperature is suitably decided depending on the starting compounds and the solvent used in the reaction, but the reaction is generally carried out at room temperature or under warming.

The resulting compound (I) of the present invention can be isolated and purified in the free form or in the form of a salt thereof by salt-forming or desalting in a conventional manner. The isolation and purification procedure may involve extraction, crystallization, recrystallization, chromatography and/or other chemical processes which are commonly employed.

The compounds (I) of the present invention and salts thereof inhibit ACAT to thereby inhibit the accumulation of cholesterol ester in the smooth muscle cells of the arterial wall. It also inhibits the absorption of cholesterol from the intestinal tract and facilitates the catabolism and excretion of cholesterol in the liver to thereby lower blood cholesterol levels and reduce the accumulation and storage of cholesterol ester in the arterial wall, which in turn inhibits the formation or progression of atherosclerotic lesions. These actions are not seen in the conventional lipid-lowering agents.

The compounds (I) and salts thereof according to the present invention have been demonstrated by animal experiments to have excellent blood total cholesterol and low-density lipoprotein (LDL) lowering effects and is useful in lowering lipids as well as in the prevention and treatment of various diseases related to arteriosclerosis, such as cerebral infarction, transient ischemic attack, angina pectoris, peripheral thrombus and arteriosclerotic obliterans.

The effects of the compound of the present invention have been confirmed in the following manner.

i) ACAT enzyme inhibiting activity:

Inhibitory action against acyl-CoA cholesterol acyltransferase (ACAT) activity in rabbit liver microsome The rabbit liver microsome was prepared as an enzyme fraction according to the method of Heider (J. G. Heider et al., J. of Lipid Res., Vol. 24, 1127–34 (1983)).

To the mixture of 0.154M phosphate buffer solution (pH 7.4), 2 mM dithiothreitol, 36 µM bovine serum albumin and 10–100 µg of microsome fraction was added liposome prepared by the method of Suckling (K. E. Suckling et al., FEBS Letters, Vol. 151, No. 111–116 (1983)) so that the proposition of liposome became 20% v/v. To the mixture was added 2% v/v of each concentration of test compound solution in dimethyl sulfoxide and the mixture was heated at 37° C. for 5 minutes. Then 36 µM oleoyl CoA containing $1^{14}C$-oleoyl CoA was added and the resultant mixture was heated at 37° C. for 10 minutes. The reaction was stopped by adding chloroform/methanol (=2/1). After stirring, cholesterol oleate extracted into the chloroform layer was separated by thin layer chromatography and the radioactivity was determined as ACAT activity. The results obtained are shown in Table 1.

TABLE 1

| Test Compound | ACAT Inhibiting Activity $IC_{50}$* |
|---|---|
| Compound of Example 1 | $7.3 \times 10^{-8}$ M |
| Compound of Example 10 | $6.1 \times 10^{-8}$ M |

*$IC_{50}$: 50% Inhibition Concentration ii) Lipid-lowering activity:

Male Sprague-Dawley rats, 5 weeks of age, were fed with a diet containing 1.5% cholesterol and 0.5% bile acid for 7 days and during the last 5 days, the compound (I) of this invention suspended in a 0.5% aqueous solution of methylcellulose was orally administered via sonde once a day. Two hours after the last administration, blood samples were collected under ether anesthesia for determination of serum total cholesterol level and HDL-cholesterol level. The cholesterol level was determined by the method of Siedel et al. (Siedel, J. et al., J. Clin. Chem. Clin. Biochem., 19,838 (1981)) and the HDL-cholesterol level was determined by the method of Ishikawa et al. (Ishikawa, T. et al., Lipids, 11, 628 (1976)). The results obtained are shown in Table 2.

TABLE 2

| Test Compound | % Reduction in Serum Total Cholesterol ED$_{50}$ |
|---|---|
| Compound of Example 1 | 3.8 mg/kg |
| Compound of Example 10 | 1.7 mg/kg |
| Compound of Example 212 in GB-A-2,113,684 | 249 mg/kg |
| Compound of Example 1 in EP-A-0,335,375 | 514 mg/kg |

As mentioned hereinbefore, another object of the present invention is to provide a pharmaceutical composition containing the compound (I) or a salt thereof.

Such pharmaceutical composition can be manufactured by formulating the compound (I) or a salt thereof with the pharmaceutically acceptable carrier, vehicle or excipient which is commonly employed in the art in accordance with the established pharmaceutical manufacturing practice.

The pharmaceutical composition of the present invention can be administered orally in such dosage forms as tablets, pills, capsules, granules, powders, solutions, etc., parenterally in the form of an injectable preparation, or otherwise, for example in the form of suppositories. The dosage depends on the symptom, the age and sex of the patient and other factors but generally the daily oral dose per adult human, for instance, is about 50 mg to about 500 mg, which can be administered in a single dose or in 2 to 4 divided doses.

The following examples are further illustrative of the present invention and should by no means be construed as defining the metes and bounds of the invention. In the examples, $^1$H-NMR stands for proton nuclear magnetic resonance. spectrum, Mass for mass spectrum, and IR for infrared absorption spectrum.

Reference Examples are also given hereinafter for describing the processes for production of the starting compounds used in the Examples.

REFERENCE EXAMPLE 1

N-Cycloheptyl-[(2-fluorenyl)methyl]amine

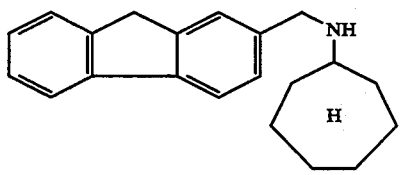

2-Formylfluorene (2.27 g, 11.7 mmol) and cycloheptylamine (1.39 g, 12.3 mmol) were heated together at 120° C. for 14 hrs. After cooling, the reaction mixture was distilled under reduced pressure. Then, ethanol (30 ml) and sodium borohydride (0.44 g, 11.7 mmol) were added to the residue and the mixture was stirred for 0.5 hr. The mixture was then diluted with water (100 ml) and extracted with chloroform (80 ml×2 times). The organic layer was dried over anhydrous magnesiumsulfate. The solvent was then distilled off under reduced pressure to give 3.15 g of a pale yellow solid residue.

$^1$H-NMR (δ ppm, in deuteriochloroform) 2.70 (1H, m), 3.79 (2H, s), 3.83 (2H, s) Mass m/z 291 (M$^+$)

The following compounds were Synthesized in generally the same manner as above.

REFERENCE EXAMPLE 2

N-Cycloheptyl-[(9-phenanthrenyl)methyl]amine

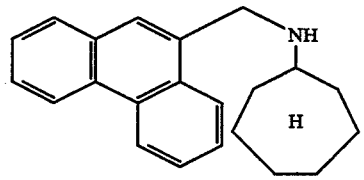

$^1$H-NMR (δ ppm, in deuteriochloroform) 2.84 (1H, m), 4.23 (2H, s), 8.65 (2H, m)

REFERENCE EXAMPLE 3

N-Cycloheptyl-(6,7,8,9-tetrahydro-5H-benzocyclohepten-yl) amine

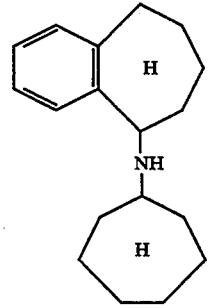

$^1$H-NMR (δ ppm, in deuteriochloroform) 3.95 (1H, m), 4.92 (1H, m), 7.10 (4H, m)

REFERENCE EXAMPLE 4

N-Cycloheptyl-[(2-phenanthrenyl)methyl]amine

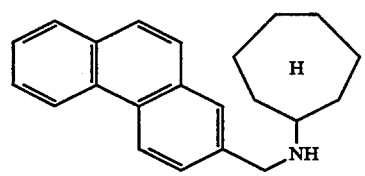

2-Methylphenanthrene (2.00 g, 10.4 mmol) was brominated with N-bromosuccinimide (2.05 g, 11.5 mmol) and the product compound was added gradually to a suspension of cycloheptylamine (2.38 g, 21.0 mmol) and potassium carbonate (2.90 μg, 21.0 mmol) in dimethylformamide (20 ml) with ice-cooling. The mixture was then stirred at room temperature for 16 hrs and, then, filtered and the filtrate was concentrated under reduced pressure. The residue was purified by silica gel column chromatography to give 2.11 g of a viscous liquid. ¹H-NMR (δ ppm, in deuteriochloroform) 2.83 (2H, m), 4.02 (2H, s), 8.68 (2H, m)

The following compound was synthesized in generally the same manner as above.

REFERENCE EXAMPLE 5

N-Cycloheptyl-[(1-phenanthrenyl)methyl]amine

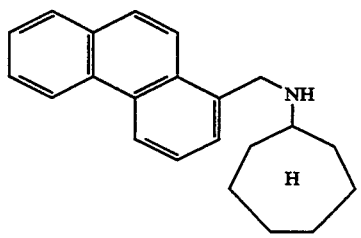

¹H-NMR δ ppm, in deuteriochloroform) 2.83 (1H, m), 4.20 (2H, s), 8.62 (2H, m) Mass m/z 303 (M+)

REFERENCE EXAMPLE 6

N-Cycloheptyl-2-fluoreneacetamide

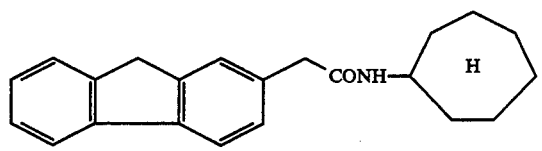

In dimethylformamide (50 ml) was dissolved 2-fluoreneacetic acid (2.24 g) followed by addition of 1-hydroxybenztriazole (2.0 g) and, then, dicyclohexylcarbodiimide (3.1 g) with constant stirring and ice-cooling. The mixture was further ,stirred at room temperature for 15 minutes. Cycloheptylamine (1.7 g) was then added under ice-cooling and the mixture was stirred at room temperature for 8 hrs. The resulting solid was filtered off and the filtrate was distilled under reduced pressure. The residue was extracted with 50 ml of chloroform and the extract was washed with 1N aqueous sodium hydroxide solution, 1N hydrochloric acid and water in the order mentioned and dried over anhydrous magnesium sulfate. The solvent was then distilled off under reduced pressure and the residue was purified by silica gel column chromatography to give 2.1 g of N-cycloheptyl-2-fluoreneacetamide as a solid.

¹H-NMR (δ ppm, in deuteriochloroform) 3.61 (2H, s), 3.90 (2H, s)

REFERENCE EXAMPLE 7

2-Cycloheptylaminoethylfluorene

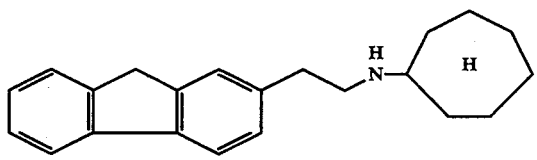

In dry tetrahydrofuran (30 ml) was dissolved 2-cycloheptylcarbamoylmethylfluorene (1.9 g) followed by dropwise addition of borane-methyl sulfide complex (1.8 ml) with ice-cooling. The mixture was then refluxed for 4 hrs, at the end of which time methanol (0.72 ml) was added with ice-cooling. The mixture was stirred at room temperature for 30 minutes, followed by addition of concentrated hydrochloric acid (1.8 ml) with ice-cooling. The mixture was refluxed again for 30 minutes. The reaction mixture was then cooled with ice and the resulting solid was recovered by filtration and washed with ether. The solid matter thus obtained was dissolved in chloroform and the solution was alkalinized with aqueous sodium hydroxide solution. The chloroform layer was taken and dried and the solvent was distilled off under reduced pressure to give 2-cycloheptylaminoethylfluorene (1.2 g).

¹H-NMR (δ ppm, in deuteriochloroform) 2.88 (4H, s), 3.86 (2H, s)

REFERENCE EXAMPLE 8

N-Cycloheptyl-[(1-fluorenyl)methyl]amine

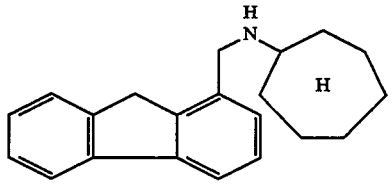

To N-cycloheptyl-1-fluorenecarboxamide (1.00 g, 3.28 mmol) was added a 1M solution of borane-tetrahydrofuran complex in THF (13 ml, 13 mmol) and the mixture was heated at 60° C. for 7.5 hrs. To this reaction mixture were added methanol (0.4 ml) and concentrated hydrochloric acid (3 ml) and the mixture was heated at 60° C. for 0.5 hr. Then, 1N aqueous sodium hydroxide solution (50 ml) was added at room temperature and the mixture was extracted with chloroform (80 ml×2 times). The organic layer was taken, dried and concentrated. To the residue were added ether (30 ml) and 4N hydrogen chloride in ethyl acetate (2 ml) and the resulting white solid was collected by filtration. This solid was dissolved in chloroform (80 ml) and washed with 1N aqueous sodium hydroxide solution (80 ml×1). The Organic layer was dried and concentrated to give 0.90 g of a pale yellow solid.

¹H-NMR (δ ppm, in deuteriochloroform) 2.71 (1H, m), 3.84 (2H, s), 3.87 (2H, s) Mass m/z 291 (M+)

The following compound was synthesized in generally the same manner as above.

REFERENCE EXAMPLE 9

N-Cycloheptyl-[(4-fluorenyl)methyl]amine

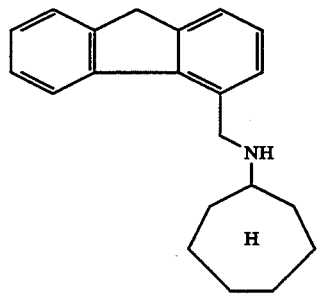

¹H-NMR (δ ppm, in deuteriochloroform) 2.86 (1H, m), 3.90 (2H, s), 4.20 (2H, s)

REFERENCE EXAMPLE 10

N-Cycloheptyl-[(2-biphenylenyl)methyl]amine

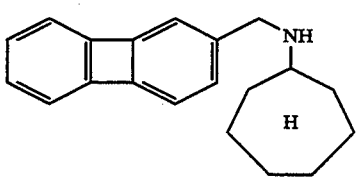

Biphenylenecarboxylic acid (1.00 g, 5.10 mmol) and a small amount of dimethylformamide were heated in 10 ml of thionyl chloride at 80° C. for 0.5 hr. After cooling, the solvent was distilled off. To the residue was added methylene chloride (30 ml), followed by gradual addition of a solution of cycloheptylamine (0.86 g, 7.6 mmol) and triethylamine (0.77 g, 7.6 mmol) in methylene chloride (20 ml) with ice-cooling. The mixture was stirred at room temperature for 1 hr, at the end of which time chloroform (50 ml) was added. The mixture was washed with water (50 ml), dried over anhydrous magnesium sulfate and concentrated under reduced pressure. The residue was purified by silica gel column chromatography to give 1.39 g of the amide as a white solid.

$^1$H-NMR ($\delta$ ppm, in deuteriochloroform) 1.58 (10H, s), 4.10 (1H, m) Mass m/z 291 (M+)

In a 1M solution of boran-tetrahydrofuran complex in THF (37 ml), 2.85 g of the above amide was heated at 65° C. for 8 hrs. To the solution was added methanol (1 ml) and concentrated hydrochloric acid (5 ml), the reaction mixture was further heated at 65° C. for 1 hr and diluted with 1N aqueous sodium hydroxide solution (100 ml). The mixture was extracted with chloroform (160 ml×2 times) and the extract was dried over anhydrous magnesium sulfate and concentrated under reduced pressure. The residue was purified by silica gel column chromatography to give 1.19 g of the amine compound.

$^1$H-NMR ($\delta$ ppm, in deuteriochloroform) 2.88 (1H, m), 3.70 (2H, s)

REFERENCE EXAMPLE 11

N-(5,6,7,8-Tetrahydronaphthyl)-O-phenylcarbamate

A solution of phenyl chloroformate (7.83 g, 50 mmol) in toluene (20 ml) was added gradually to a solution of 5,6,7,8-tetrahydronaphthylamine (7.36 g, 50 mmol) and triethylamine (6.07 g, 60 mmol) in toluene (100 ml) under ice-cooling. The mixture was then stirred at room temperature for 1 hr, followed by addition of ethyl acetate (100 ml). The mixture was washed with water (100 ml), dried over anhydrous magnesium sulfate and concentrated under reduced pressure. The residue was washed with hexane and the resulting white solid was collected by filtration to give 8.08 g of the carbamate.

$^1$H-NMR ($\delta$ ppm, in deuteriochloroform) 1.90 (4H, m), 2.70 (4H, m), 7.64 (1H, d) Mass m/z 267 (M+)

REFERENCE EXAMPLE 12

N-Cycloheptyl-1-(2-fluorenyl)ethylamine

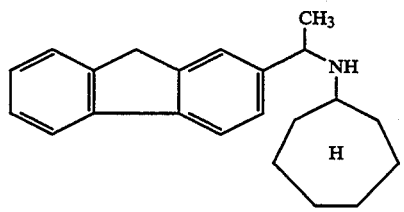

2-Acetylfluorene (4.17 g, 20 mmol) and cycloheptylamine (2.38 g, 21 mmol) were heated together at 130° C. for 14 hrs and, then, distilled under reduced pressure. To the residue were added ethanol (20 ml) and sodium borohydride (0.76 g, 20 mmol) and the mixture was stirred at room temperature overnight. The mixture was then diluted with water (100 ml) and extracted with chloroform (80 ml×2 times). The organic layer was dried over anhydrous magnesium sulfate and concentrated. The residue was then purified by silica gel column chromatography to give 1.58 g of the amine compound.

$^1$H-NMR ($\delta$ ppm, in deuteriochloroform) 2.52 (1H, m), 3.76 (2H, s)

The following compound was synthesized in generally the same manner as above.

REFERENCE EXAMPLE 13

N-(Exo-2-norbornyl)-(9-phenanthrenyl)methylamine

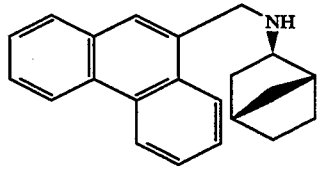

$^1$H-NMR ($\delta$ ppm, in deuteriochloroform) 2.28 (2H, m), 2.77 (1H, m), 4.20 (2H, m) Mass m/z 301 (M+)

EXAMPLE 1

1-Cycloheptyl-1-[(2-fluorenyl)methyl]-3-(2,4,6-trimethylphenyl)urea

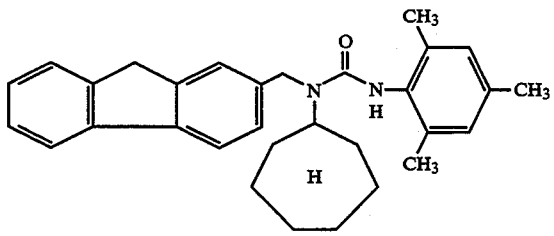

A mixture of N-cycloheptyl-[(2-fluorenyl)methyl]amine (980 mg, 3.36 mmol) and N-(2,4,6-trimethylphenyl)-o-phenylcarbamate (820 mg, 3.2 mmol) in toluene (10 ml) was refluxed for 15 hrs.

The reaction mixture was then diluted with toluene (50 ml) and washed with 1N aqueous sodium hydroxide solution (50 ml×2 times).

The organic layer was dried over anhydrous. magnesium sulfate and concentrated. From the residue was obtained 940 mg of a white solid.

m.p. 124°–126° C. $^1$H-NMR (δ ppm, in deuteriochloroform) 1.96 (6H, s), 3.89 (2H, s), 4.58 (2H, s), 6.76 (2H, s) Elemental analysis (for $C_{31}H_{36}N_2O$) Found: C, 82.47%; H, 8.08%; N, 6.16% Calcd.: C, 82.26%; H, 8.02%; N, 6.19%

The following compounds were synthesized in generally the same manner as above.

EXAMPLE 2

1-Cycloheptyl-1-(6,7,8,9-tetrahydro-5H-benzocyclohepten-5-yl)-3-(2,4,6-trifluorophenyl)urea

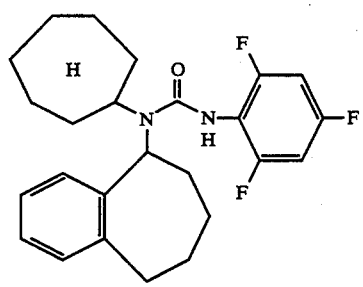

IR (cm$^{-1}$, KBr tablet) 1640, 1520, 1450, 1120 $^1$H-NMR (δ ppm, in deuteriochloroform) 4.43 (1H, m), 4.70 (1H, m), 6.67 (2H, m) Mass (FAB) m/z 431 (M$^+$+1)

EXAMPLE 3

1-Cycloheptyl-1-[(9-anthracenyl)methyl]-3-(2,4,6-trifluorophenyl)urea

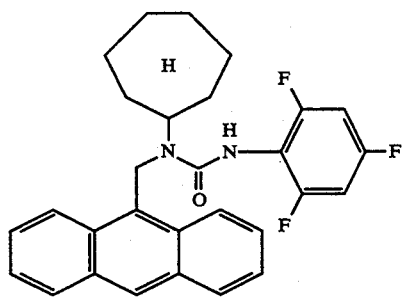

m.p. 175°–177° C. H-NMR (δ ppm, in deuteriochloroform) 3.21 (1H, m), 5.67 (2H, s), 8.48 (.1H, s) Elemental analysis (for $C_{29}H_{27}N_2OF_3$) Found: C, 73.07%; H, 5.81%; N, 5.83%, F, 11.97% Calcd.: C, 73.09%; H, 5.71%; N, 5.88%; F, 11.96%

EXAMPLE 4

1-Cycloheptyl-1-(9-fluorenyl)-3-(2,4,6-trifluorophenyl)urea

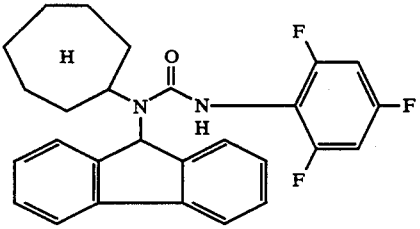

IR (cm$^{-1}$, KBr tablet) 1650, 1520, 1460, 1120
$^1$H-NMR (δ ppm, in deuteriochloroform) 4.62 (1H, m), 4.77 (1H, m), 6.42 (2H, m) Mass (FAB) m/z (M$^+$+1)

EXAMPLE 5

1-Cycloheptyl-1-[(2-fluorenyl)methyl]-3-(2,4,6-trifluorophenyl)urea

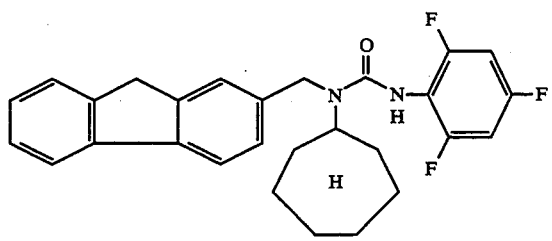

IR (cm$^{-1}$, KBr tablet) 1640, 1520, 1450, 1120 $^1$H-NMR (δ ppm, in deuteriochloroform) 3.85 (2H, s), 4.35 (1H, m), 4.55 (2H, s) 6.54 (2H, m) Mass (FAB) m/z 465 (M$^+$+1)

EXAMPLE 6

1-Cycloheptyl-1-[(9-phenanthrenyl)methyl]-3-(2,4,6-trifluorophenyl)urea

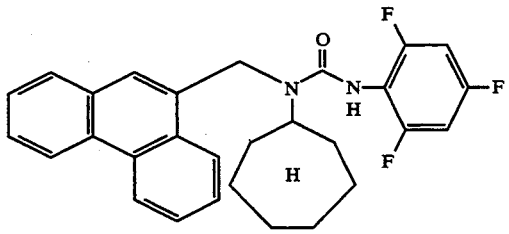

IR (cm$^{-1}$, KBr tablet) 1640, 1520, 1450, 1120 $^1$H-NMR (δ ppm, in deuteriochloroform) 4.50 (1H, m), 4.85 (2H, d), 6.51 (2H, m), 8.60 (2H, m) Mass (FAB) m/z 477. (M$^+$+1)

EXAMPLE 7

1-Cycloheptyl-1-[(9-phenanthrenyl)methyl]-3-(4-propylphenyl)urea

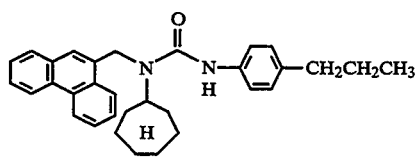

IR (cm$^{-1}$, KBr tablet) 1650, 1520, 1250, 750 $^1$H-NMR (δ ppm, in deuteriochloroform) 0.83 (3H, t), 2.42 (2H, t), 4.48 (1H, m), 4.88 (2H, s) Mass (FAB) m/z 465 (M$^+$+1)

EXAMPLE 8

1-Cycloheptyl-1-[(2-fluorenyl)methyl]-3-(4-t-butylphenyl)urea

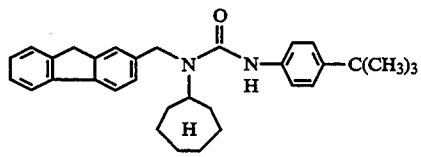

IR (cm$^{-1}$, KBr tablet) 1660, 1540, 1420, 1330 $^1$H-NMR (δ ppm, in deuteriochloroform) 1.23 (9H, s), 3.90 (2H, s), 4.54 (2H, s) Mass (FAB) m/z 467 (M$^+$+1)

EXAMPLE 9

1-Cycloheptyl-1-[(2-fluorenyl)methyl]-3-(2,6-dimethylphenyl)urea

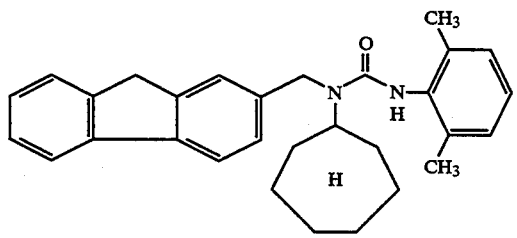

IR (cm$^{-1}$, KBr tablet) 1650, 1510, 1470, 760 H-NMR (δ ppm, in deuteriochloroform) 2.00 (6H, s), 3.90 (2H, s), 4.60 (2H, s), 6.95 (3H, s) Elemental analysis (for C$_{30}$H$_{34}$N$_2$O) Found: C, 82.18%; H, 7.94%; N, 6.22% Calcd.: C, 82.15%, H, 7.81%; N, 6.39%

EXAMPLE 10

1-Cycloheptyl-1-[(9-phenanthrenyl)methyl]-3-(2,4,6-trimethylphenyl)urea

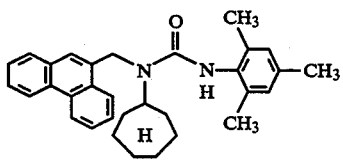

m.p. 108°–110° C. $^1$H-NMR (δ ppm, in deuteriochloroform) 2.06 (6H, s), 4.60 (1H, m), 5.00 (2H, s), 6.76 (2H, s) Elemental analysis (for C$_{32}$H$_{36}$N$_2$O) Found: C, 82.51%; H, 8.02%; N, 5.93% Calcd.: C, 82.72%; H, 7.81%; N, 6.03%

EXAMPLE 11

1-Cycloheptyl-1-[(2-fluorenyl)methyl]-3-(2,6-diethylphenyl)urea

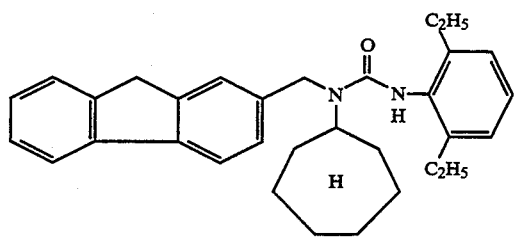

m.p. 134°–135° C.

$^1$H-NMR (δ ppm, in deuteriochloroform) 1.09 (6H, t), 2.50 (4H, q), 4.00 (2H, s) 4.69 (2H, s) Elemental analysis (for C$_{32}$H$_{38}$N$_2$O) Found: C, 82.35%; H, 8.21%; N, 5.90% Calcd.: C, 82.36%; H, 8.21%; N, 6.00%

EXAMPLE 12

1-Cycloheptyl-1-[(2-fluorenyl)methyl]-3-(2,6-diisopropylphenyl)urea

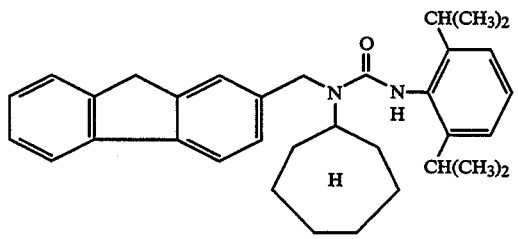

IR (cm$^{-1}$, KBr tablet) 1650, 1500, 1470, 1240 $^1$H-NMR (δ ppm, in deuteriochloroform) 2.98 (2H, m), 4.00 (2H, s), 4.70 (2H, s) Mass (FAB) 495 (M+1)

EXAMPLE 13

1-Cycloheptyl-1-[(2-phenanthrenyl)methyl]-3-(2,4,6-trifluorophenyl)urea

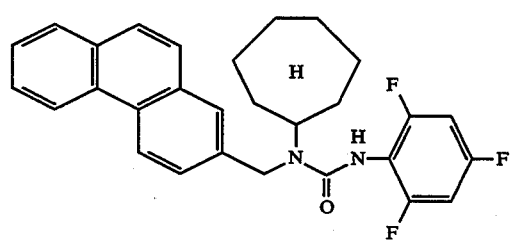

IR (cm$^{-1}$, KBr tablet) 1640, 1520, 1120, 750 $^1$H-NMR (δ ppm, in deuteriochloroform) 4.43 (1H, m), 4.74 (2H, s) 6.58 (2H, m) Mass (FAB) m/z 477 (M$^+$+1).

EXAMPLE 14

1-Cycloheptyl-1-[(2-phenanthrenyl)methyl]-3-(2,4 6-trimethylphenyl) urea

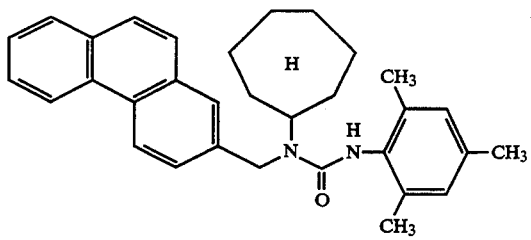

m.p. 120°-122° C. IR (cm$^{-1}$, KBr tablet) 1630, 1510, 1260, 810 $^1$H-NMR (δ ppm, in deuteriochloroform) 1.94 (6H, s), 4.70 (2H, s), 6.72 (2H, s) Mass (FAB)m/z 465 (M$^+$+1)

EXAMPLE 15

1-Cycloheptyl-1-[(1-phenanthrenyl)methyl]-3-(2,4,6-trimethylphenyl) urea

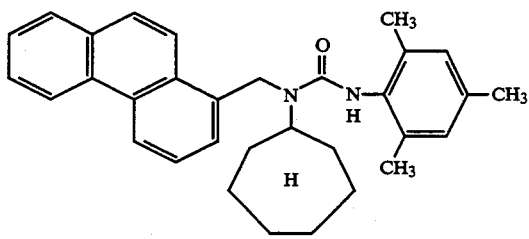

m.p. 163°-165° C. $^1$H-NMR (δ ppm, in deuteriochloroform) 2.06 (6H, s), 5.05 (2H, s), 6.77 (2H, s) Elemental analysis: (for C$_{32}$H$_{36}$N$_2$O) Found: C, 82.54%; H, 7.97%; N, 5.86% Calcd.: C, 82.72%; H, 7.81%; N, 6.03%

EXAMPLE 16

1-Cycloheptyl-1-[(1-phenanthrenyl)methyl]-3-(2,4,6-trifluorophenyl)urea

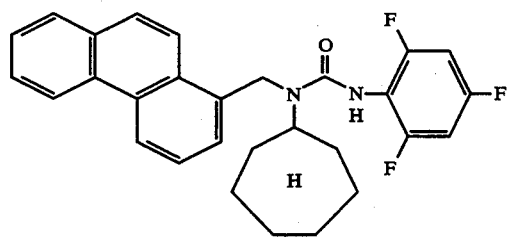

IR (cm$^{-1}$, KBr tablet) 1650, 1520, 1120, 750 $^1$H-NMR (δ ppm, in deuteriochloroform) 4.44 (1H, m), 5.05 (2H, s), 6.62 (2H, m) Mass (FAB) m/z 477 (M$^+$+1)

EXAMPLE 17

1-Cycloheptyl-[(1-fluorenyl)methyl]-3-(2,4,6-trimethylphenyl)urea

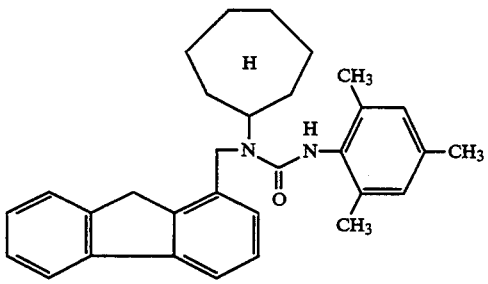

m.p. 183°-184° C. $^1$H-NMR (δ ppm, in deuteriochloroform) 2.00 (6H, s), 3.83 (2H, s), 4.58 (2H, s) Elemental analysis (for C_H$_3$N$_2$O) Found: C, 82.01%; H, 8.06%; N, 6.25% Calcd.: C, 82.26%; H, 8.02%; N, 6.19%

EXAMPLE 18

1-Cycloheptyl-[(4-fluorenyl)methyl]-3-(2,4,6-trimethylphenyl)urea

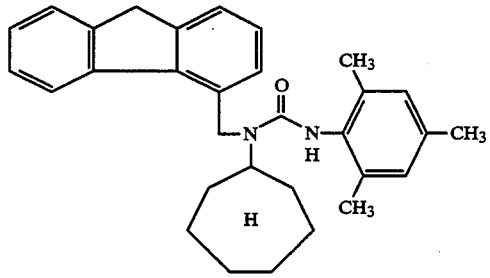

m.p. 133°-136° C. $^1$H-NMR (δ ppm, in deuteriochloroform) 2.04 (6H, s), 3.95 (2H, s), 4.97 (2H, s) Elemental analysis (for C$_{31}$H$_{36}$N$_2$O) Found: C, 82.02%; H, 8.14%; N, 5.94% Calcd.: C, 82.26%; H, 8.02%; N, 6.19%

EXAMPLE 19

1-Cycloheptyl-1-[(2-fluorenyl)ethyl]-3-(2,4,6-trimethylphenyl)urea

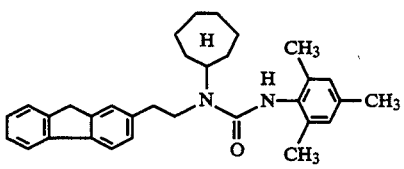

IR (cm$^{-1}$, KBr tablet) 2936, 1632, 1494 $^1$H-NMR (δ ppm, in deuteriochloroform) 2.12 (6H, s), 2.22 (3H, s), 3.00 (2H, t), 3.52 (2H, t), 3.84 (2H, s) Mass (FAB) m/z 467 (M$^+$+1)

EXAMPLE 20

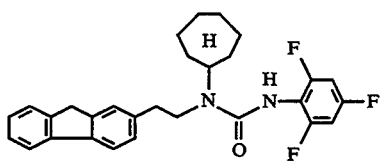

1-Cycloheptyl-1-[(2-fluorenyl)ethyl]-3-(2,4,6-trifluorophenyl)urea

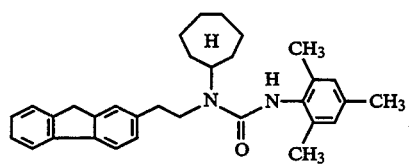

IR (cm$^{-1}$, KBr tablet) 1638, 1522, 1452, 1120, 1044
$^{1}$H-NMR (δ ppm, in deuteriochloroform) 3.00 (2H, t), 3.52 (2H, t), 3.84 (2H, s) Mass (FAB) m/z 479 (M$^{+}$+1)

EXAMPLE 21

1-Cycloheptyl-1-(6,7,8,9-tetrahydro-5H-benzocyclohepten-5-yl)-3-[p-(N,N-dimethylamino)phenyl]urea monohydrochloride

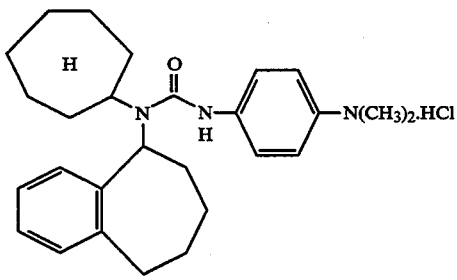

N-Cycloheptyl-(6,7,8,9-tetrahydro-5H-benzocycloheptenyl)amine (0.8 g, 3.1 mmol) and 4-(N,N-dimethyamino)phenylisocyanate (0.50 g, 3.1 mmol) was stirred in dichloromethane (10 ml) at room temperature for 18 hrs. The reaction mixture was then purified by silica gel column chromatography. The resulting urea compound was treated with hydrochloric acid in ether to give 0.72 g of the above hydrochloride compound.

IR (cm$^{-1}$, KBr tablet) 1660, 1520, 1320 $^{1}$H-NMR (δ ppm, in deuteriochloroform) 3.13 (6H, s), 4.40 (1H, m), 7.2–7.5 (8H, m) Mass (FAB) m/z 421 (M$^{+}$+1)

EXAMPLE 22

1-Cycloheptyl-1-[(2-biphenylenyl)methyl]-3-(2,4,6-trimethylphenyl)urea

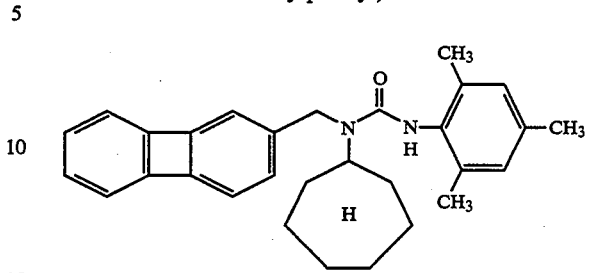

N-Cycloheptyl-(2-biphenylenyl)methylamine (1.10 g, 3.96 mmol) and N-(2,4,6-trimethylphenyl)-0-phenylcarbamate (0.77 g, 3.00 mmol) was refluxed in toluene (10 ml) for 24 hrs. The reaction mixture was then diluted with toluene (50 ml), washed with 1N aqueous sodium hydroxide solution (50 ml×2 times), dried over anhydrous magnesium sulfate and concentrated under reduced pressure. The residue was purified by silica gel column chromatography to give 0.83 g of the urea compound.

m.p. 123°–124° C. IR (cm$^{-1}$, KBr tablet) 1630, 1510, 740 $^{1}$H-NMR (δ ppm, in deuteriochloroform) 2.05 (6H, s), 2.20 (3H, s), 4.24 (2H, s) Mass (FAB) m/z 439 (M$^{+}$+1)

The following compounds were synthesized in generally the same manner as above.

EXAMPLE 23

1-Cycloheptyl-1-[1-(2-fluorenyl)ethyl]-3-(2,4,6-trimethylphenyl)urea

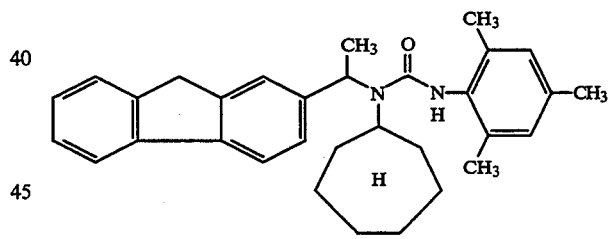

IR (cm$^{-1}$, KBr tablet) 1650, 1500, 1240, 740 $^{1}$H-NMR (δ ppm, in deuteriochloroform) 2.03 (6H, s), 3.88 (2H, s) Mass (FAB) m/z 467 (M$^{+}$+1)

EXAMPLE 24

1-(Exo-2-norbornyl)-1-[(9-phenanthrenyl)methyl]-3-[1(5,6,7,8-tetrahydronaphthyl)]urea

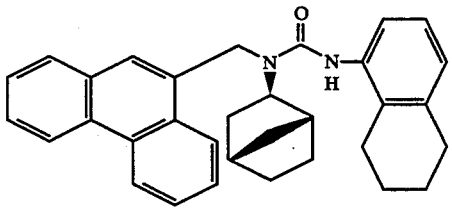

IR (cm$^{-1}$, KBr tablet) 1650, 1530, 1230, 750 $^{1}$H-NMR (δ ppm, in deuteriochloroform) 2.60 (2H, m), 5.14 (2H, s) Mass (FAB) m/z 475 (M$^{+}$+1)

EXAMPLE 25

1-Cyclohexyl-1-[(9-phenanthrenyl)methyl]-3-(2,4,6-trifluorophenyl)urea

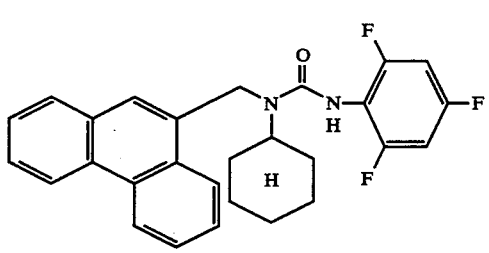

A mixture of N-cyclohexyl-N-(9-phenanthrenylmethyl)amine (0.90 g) and N-(2,4,6-trifluorophenyl)-o-phenylcarbamate (0.80 g) in toluene (10 ml) was refluxed for 17 hrs. After cooling, the reaction mixture was diluted with toluene (80 ml). The organic layer was washed with 1N aqueous sodium hydroxide solution- (80 ml×2 times), dried over anhydrous magnesium sulfate, and concentrated under reduced pressure. The residue was crystallized from hexane-ether, and the resulting solid was collected by filtration and dried to give 1.01 g of 1-cyclohexyl-1-[(9phenanthrenyl)methyl]-3-(2,4,6-trifluorophenyl)urea.

m.p. 122°–124° C. IR (cm$^{-1}$, KBr tablet) 3340, 1665, 1650, 1325, 1125, 1045, 755 $^1$H-NMR (6 ppm, in deuteriochloroform) 0.9–2.0 (10H), 4.50 (1H, m), 5.02 (2H, s), 5.76 (1H, s), 6.60 (2H, t), 7.6–8.1 (7H), 8.6–8.8 (2H, m)

The following compounds were synthesized in generally the same manner as above.

EXAMPLE 26

1-Cyclohexyl-1-[(9-phenanthrenyl)methyl]-3-(2,4,6-trimethylphenyl)urea

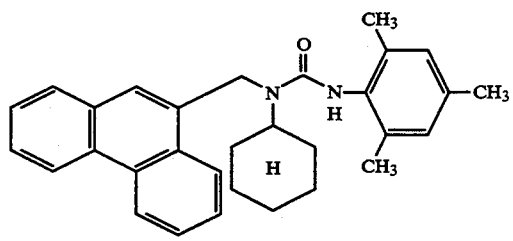

m.p. 125°–128° C. IR (cm$^{-1}$, KBr tablet) 3340, 1655, 1635, 1500, 1245, 750 $^1$H-NMR (6 ppm, in deuteriochloroform) 0.9–2.0 (10H), 2.03 (6H, s), 2.17 (3H, s), 4.54 (1H, m), 5.02 (2H, s), 5.64 (1H, s), 6.74 (2H, s), 7.5–8.1 (7H, m), 8.6–8.8 (2H, m) Elemental analysis (for C$_{31}$H$_{34}$N$_2$O) Found: C, 82.79%; H 7.75%; N, 6.21% Calcd.: C, 82.63%; H, 7.61%; N, 6.22%

EXAMPLE 27

1-Cyclohexyl-1-[(2-fluorenyl)methyl]-3-(2,4,6-trifluorophenyl)urea

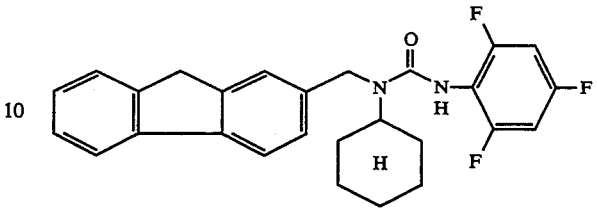

m.p. 162°–165° C. IR (cm$^{-1}$, KBr tablet) 3250, 1640, 1530, 1460, 1125, 1450, 840 $^1$H-NMR (6 ppm, in deuteriochloroform) 1.0–2.0 (10H, m), 3.90 (2H, s), 4.34 (1H, m), 4.62 (2H, s), 5.64 (1H, s), 6.60 (2H, t) 7.2–7.8 (7H, m,) Elemental analysis (for C$_{27}$H$_{25}$N$_2$OF$_3$) Found: C, 72 02%; H, 5 72% N, 6 07% F 12.42% Calcd.: C, 71.99%; H, 5.59%; N, 6.22%; F, 12.65%

EXAMPLE 28

1-Cyclohexyl-1-[(2-fluorenyl)methyl]-3-(2,4,6trimethylphenyl)urea

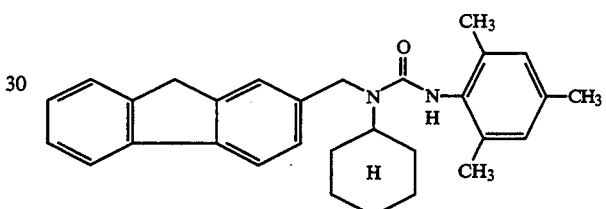

m. p. 147°–149° C. IR (cm$^{-1}$, KBr tablet) 3330, 1630, 1510, 1245, 765, 735 $^1$H-NMR (6 ppm, in deuteriochloroform) 1.0–2.0 (10H, m), 1.95 (6H, s), 2.17 (3H, s), 3.87 (2H, s), 4.40 (1H, m), 4.57 (2H, s), 5.56 (1H, s), 6.76 (2H, s), 7.2–7.8 (7H, m) Elemental analysis (for C$_{30}$H$_{34}$N$_2$O) Found: C, 82.09%; H, 7.87%; N, 6.30% Calcd.: C, 82.15%; H, 7.82L%; N, 6.39%

While the invention has been described in detail and with reference to specific embodiments thereof, it will be apparent to one skilled in the art that various changes and modifications can be made therein without departing from the spirit and scope thereof.

What is claimed is:

1. An urea derivative of the formula (I):

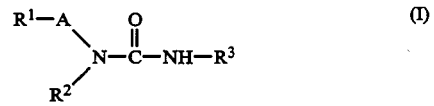

wherein R$^1$ represents a condensed carbocyclic group containing at least 11 carbon atoms; R$^2$ represents a cycloalkyl group which may optionally have a bridgehead; R$^3$ represents a phenyl group which may optionally be substituted by one or more substituents selected from the group consisting of halogens, lower alkyl groups, amino, and mono- or di-lower alkylamino groups or a tetrahydronaphthyl group; A represents a single bond or a straight-chain or branched alkylene group containing 1 to 6 carbon atoms, or a salt thereof.

2. An urea derivative or a salt thereof as claimed in claim 1, wherein R$^1$ in formula (I) is a fluorenyl group.

3. An urea derivative or a salt thereof as claimed in claim 1, wherein $R^1$ in formula (I) is a phenanthrenyl group.

4. An urea derivative or a salt thereof as claimed in claim 1, wherein $R^1$ in formula (I) is a fluorenyl group and $R^3$ in formula (I) is a phenyl group which is substituted by three lower alkyl groups.

5. 1-Cycloheptyl-1-(2-fluorenylmethyl)-3-(2,4,6-trimethylphenyl)urea or a salt thereof.

6. 1-Cycloheptyl-1-(9-phenanthrenylmethyl)-3-(2,4,6-trimethylphenyl)urea or a salt thereof.

7. A pharmaceutical composition comprising a therapeutically effective amount of an urea derivative of the formula (I)

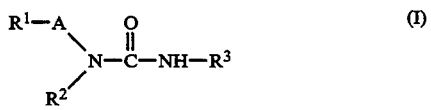

wherein $R^1$ represents a condensed carbocyclic group containing at least 11 carbon atoms; $R^2$ represents a cycloalkyl group which may optionally have a bridgehead; $R^3$ represents a phenyl group which may optionally be substituted by one or more substituents selected from the group consisting of halogens, lower alkyl groups, amino, and mono- or di-lower alkylamino groups or a tetrahydronaphthyl group; A represents a single bond or a straight-chain or branched alkylene group containing 1 to 6 carbon atoms, or a salt thereof, and a pharmaceutically acceptable-carrier.

8. The pharmaceutical composition as claimed in claim 7, wherein $R^1$ in formula (I) is a fluorenyl group.

9. The pharmaceutical composition as claimed in claim 7, wherein $R^1$ in formula (I) is a phenanthrenyl group.

10. The pharmaceutical composition as claimed in claim 7, wherein $R^1$ in formula (I) is a fluorenyl group and $R^3$ in formula (I) is a phenyl group which is substituted by three lower alkyl groups.

11. The pharmaceutical composition as claimed in claim 8 wherein the urea derivative is 1-Cyclohepthyl-1-(2-fluorenylmethyl)-3-(2,4,6-trimethylphenyl)urea or a salt thereof.

12. The pharmaceutical composition as claimed in claim 9 wherein the urea derivative is 1-Cyclohepthyl-1-(9-phenanthrenylmethyl)-3(2,4,6-trimethylphenyl)urea or a salt thereof.

* * * * *